US012697187B2

(12) United States Patent
Pickering et al.

(10) Patent No.: US 12,697,187 B2
(45) Date of Patent: Aug. 4, 2026

(54) DEVICES AND SYSTEMS FOR ULTRASOUND GUIDED ENDOSCOPIC SURGICAL PROCEDURES

(71) Applicant: Covidien LP, Mansfield, MA (US)

(72) Inventors: Chad A. Pickering, Woburn, MA (US); Arvind Rajagopalan Mohan, Dracut, MA (US)

(73) Assignee: Covidien LP, Mansfield, MA (US)

( * ) Notice: Subject to any disclaimer, the term of this patent is extended or adjusted under 35 U.S.C. 154(b) by 85 days.

(21) Appl. No.: 18/499,164

(22) Filed: Oct. 31, 2023

(65) Prior Publication Data

US 2024/0341898 A1     Oct. 17, 2024

Related U.S. Application Data

(60) Provisional application No. 63/459,372, filed on Apr. 14, 2023.

(51) Int. Cl.
| | |
|---|---|
| *A61B 8/00* | (2006.01) |
| *A61B 1/303* | (2006.01) |
| *A61B 8/12* | (2006.01) |
| *A61B 90/00* | (2016.01) |

(52) U.S. Cl.
CPC .............. *A61B 90/08* (2016.02); *A61B 1/303* (2013.01); *A61B 8/12* (2013.01); *A61B 8/4209* (2013.01)

(58) Field of Classification Search
CPC .......... A61B 90/08; A61B 1/303; A61B 8/12; A61B 8/4209; A61B 46/10; A61B 2017/00477; A61B 2017/4216; A61B 2090/378; A61B 8/4422; A61B 1/00142; A61B 8/445; A61B 17/42
See application file for complete search history.

(56) References Cited

U.S. PATENT DOCUMENTS

| | | |
|---|---|---|
| 4,877,033 A | 10/1989 | Seitz, Jr. |
| 5,166,787 A | 11/1992 | Irion |
| 5,351,678 A | 10/1994 | Clayton |
| 5,935,057 A | 8/1999 | Lichtman et al. |
| 6,156,006 A | 12/2000 | Brosens et al. |
| 6,174,307 B1 | 1/2001 | Daniel et al. |

(Continued)

OTHER PUBLICATIONS

Extended European Search Report issued in corresponding European Application No. 24169416.5 dated Jul. 11, 2024,10 pages.

*Primary Examiner* — Michael J Carey
*Assistant Examiner* — Zainab Mohammed Aldarraji
(74) *Attorney, Agent, or Firm* — Carter, DeLuca & Farrell, LLP

(57)     ABSTRACT

A surgical system includes a protective cover, an ultrasound device, and a surgical device. The protective cover includes a body configured to receive at least a portion of an ultrasound device through an open proximal end and into the interior volume of the body. A coupling assembly includes an inner coupler disposed within the interior volume of the body on an interior surface of the body and an outer coupler disposed on an exterior surface of the body. The inner coupler is configured to couple to the ultrasound device and the outer coupler is configured to couple to the surgical device to thereby constrain the ultrasound device and the surgical device in at least one degree of freedom while permitting movement of the surgical device relative to the ultrasound device in at least one other degree of freedom.

15 Claims, 8 Drawing Sheets

(56) References Cited

U.S. PATENT DOCUMENTS

| | | | |
|---|---|---|---|
| 6,210,330 B1 | 4/2001 | Tepper | |
| 6,884,219 B1 | 4/2005 | Pruter | |
| 6,896,657 B2 | 5/2005 | Willis | |
| 6,908,433 B1 | 6/2005 | Pruter | |
| 6,936,048 B2 | 8/2005 | Hurst | |
| 6,960,166 B1 | 11/2005 | Wong et al. | |
| 7,517,346 B2 | 4/2009 | Sloan et al. | |
| 7,520,856 B2 | 4/2009 | Vaezy et al. | |
| 7,591,785 B2 | 9/2009 | Wendlandt et al. | |
| 7,621,869 B2 | 11/2009 | Ratnakar | |
| 7,815,571 B2 | 10/2010 | Deckman et al. | |
| 7,874,986 B2 | 1/2011 | Deckman et al. | |
| 7,918,795 B2 | 4/2011 | Grossman | |
| 8,088,072 B2 | 1/2012 | Munrow et al. | |
| 8,206,300 B2 | 6/2012 | Deckman et al. | |
| 8,262,574 B2 | 9/2012 | Placek et al. | |
| 8,262,577 B2 | 9/2012 | Munrow et al. | |
| 8,298,145 B2 | 10/2012 | Deckman et al. | |
| 8,506,485 B2 | 8/2013 | Deckman et al. | |
| 8,992,427 B2 | 3/2015 | Munrow et al. | |
| 9,357,977 B2 | 6/2016 | Grossman | |
| 9,517,047 B2 | 12/2016 | Grossman | |
| 9,808,310 B2 | 11/2017 | Grossman | |
| 9,861,336 B2 | 1/2018 | Munrow et al. | |
| 9,987,080 B2 | 6/2018 | Grossman | |
| 10,058,342 B2 | 8/2018 | Deckman et al. | |
| 10,182,862 B2 | 1/2019 | Grossman | |
| 10,321,951 B2 | 6/2019 | Placek et al. | |
| 10,595,819 B2 | 3/2020 | Deckman et al. | |
| 10,610,197 B2 | 4/2020 | Deckman et al. | |
| 10,750,939 B2 | 8/2020 | Begg | |
| 2004/0153105 A1 | 8/2004 | Burbank et al. | |
| 2004/0158262 A1 | 8/2004 | Burbank et al. | |
| 2004/0181152 A1 | 9/2004 | Zhang et al. | |
| 2005/0203399 A1 | 9/2005 | Vaezy et al. | |
| 2005/0234294 A1 | 10/2005 | Saadat et al. | |
| 2005/0272975 A1 | 12/2005 | McWeeney et al. | |
| 2006/0004410 A1 | 1/2006 | Nobis et al. | |
| 2006/0189972 A1 | 8/2006 | Grossman | |
| 2007/0112272 A1 | 5/2007 | Park et al. | |
| 2007/0213749 A1 | 9/2007 | Kogasaka | |
| 2007/0244353 A1 | 10/2007 | Larsen | |
| 2007/0249939 A1 | 10/2007 | Gerbi et al. | |
| 2009/0259097 A1 | 10/2009 | Thompson | |
| 2009/0318758 A1 | 12/2009 | Farr et al. | |
| 2011/0160535 A1 | 6/2011 | Bayer et al. | |
| 2012/0116248 A1 | 5/2012 | Mcweeney et al. | |
| 2012/0245416 A1 | 9/2012 | Viola | |
| 2013/0046137 A1 | 2/2013 | Zhao et al. | |
| 2014/0100558 A1 | 4/2014 | Schmitz et al. | |
| 2014/0180001 A1 | 6/2014 | von Grunberg et al. | |
| 2014/0228875 A1 | 8/2014 | Saadat | |
| 2014/0276081 A1 | 9/2014 | Tegels | |
| 2016/0287210 A1 | 10/2016 | Chumo et al. | |
| 2017/0049548 A1 | 2/2017 | Harari et al. | |
| 2017/0245838 A1 | 8/2017 | Munrow et al. | |
| 2017/0245891 A1 | 8/2017 | Munrow et al. | |
| 2017/0290626 A1 | 10/2017 | Deckman et al. | |
| 2017/0290627 A1 | 10/2017 | Deckman et al. | |
| 2017/0304095 A1* | 10/2017 | Syed | A61B 17/221 |
| 2017/0319174 A1 | 11/2017 | Hill et al. | |
| 2017/0340308 A1 | 11/2017 | Cermak et al. | |
| 2018/0008237 A1 | 1/2018 | Venkataraman et al. | |
| 2018/0042572 A1 | 2/2018 | Munrow et al. | |
| 2018/0078303 A1 | 3/2018 | Grossman | |
| 2018/0132927 A1 | 5/2018 | Chen et al. | |
| 2018/0206712 A1 | 7/2018 | Begg | |
| 2018/0318026 A1 | 11/2018 | Placek | |
| 2019/0142370 A1 | 5/2019 | Roy et al. | |
| 2019/0192217 A1 | 6/2019 | Grossman | |
| 2019/0262080 A1 | 8/2019 | Hammudi et al. | |
| 2019/0269456 A1 | 9/2019 | Placek et al. | |
| 2019/0350648 A1 | 11/2019 | Owens et al. | |
| 2020/0229892 A1 | 7/2020 | Munrow et al. | |
| 2020/0275975 A1 | 9/2020 | Chen | |
| 2021/0204910 A1* | 7/2021 | Begg | A61B 8/0841 |
| 2023/0023910 A1* | 1/2023 | Peterson | A61B 8/4455 |

* cited by examiner

DEVICES AND SYSTEMS FOR ULTRASOUND GUIDED ENDOSCOPIC SURGICAL PROCEDURES

CROSS-REFERENCE TO RELATED APPLICATION

This application claims the benefit of, and priority to, U.S. Provisional Patent Application No. 63/459,372, filed on Apr. 14, 2023, the entire contents of which are hereby incorporated herein by reference.

FIELD

The present disclosure relates to ultrasound guided endoscopy and, more particularly, to devices and systems for ultrasound guided endoscopic surgical procedures such as transvaginal ultrasound guided hysteroscopic surgical procedures.

BACKGROUND

Transvaginal hysteroscopy includes both intrauterine procedures, e.g., procedures performed within the uterine cavity, and intramural procedures, e.g., procedures performed within the uterine wall. Intrauterine procedures may require different approaches and/or instruments as compared to intramural procedures, and vice versa. Even within the same category, hysteroscopy procedures may require different approaches and/or instruments depending upon, for example, the procedure to be performed, patient anatomy, technique utilized, and/or other considerations.

SUMMARY

As used herein, the term "distal" refers to the portion that is being described which is farther from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is a protective cover for an ultrasound device. The protective cover includes a body and a coupling assembly. The body defines an interior volume and includes a closed distal end and an open proximal end. The body is configured to receive at least a portion of an ultrasound device through the open proximal end and into the interior volume to protect the ultrasound device during insertion into a surgical site. The coupling assembly includes an inner coupler disposed within the interior volume of the body on an interior surface of the body and an outer coupler disposed on an exterior surface of the body. The inner coupler is configured to couple to the ultrasound device within the interior volume of the body and the outer coupler is configured to couple to a surgical device exteriorly of the body. The inner and outer couplers are further coupled to one another with the body disposed therebetween to thereby constrain the ultrasound device and the surgical device in at least one degree of freedom. In aspects, the inner and outer couplers are coupled to one another with the body disposed therebetween to permit movement of the surgical device relative to the ultrasound device in at least one other degree of freedom. In other aspects, the inner and outer couplers are coupled to one another with the body disposed therebetween to constrain the ultrasound device and the surgical device in all degrees of freedom.

In an aspect of the present disclosure, the inner coupler includes a first engagement interface configured to releasably engage an engagement interface associated with the ultrasound device. The first engagement interface may be a mechanical engagement interface, although other engagement interfaces such as magnetic or adhesive engagement interfaces are also contemplated.

In another aspect of the present disclosure, the outer coupler includes a second engagement interface configured to releasably engage an engagement interface associated with the surgical device. The second engagement interface may be a mechanical engagement interface, although other engagement interfaces such as magnetic or adhesive engagement interfaces are also contemplated.

In yet another aspect of the present disclosure, the inner and outer couplers are fixedly engaged with one another with the body disposed therebetween.

A surgical system provided in accordance with the present disclosure includes a protective cover, an ultrasound device, and a surgical device. The protective cover includes a body, an inner coupler disposed within an interior volume of the body on an interior surface of the body, and an outer coupler disposed on an exterior surface of the body. The ultrasound device is configured for insertion into the interior volume of the body of the protective cover and is configured to couple to the inner coupler within the interior volume of the body of the protective cover. The surgical device is configured to couple to the outer coupler exteriorly of the protective cover. The inner and outer couplers are engaged to one another with the body of the protective cover disposed therebetween such that, with the ultrasound device coupled to the inner coupler and the surgical device coupled to the outer coupler, the ultrasound device and the surgical device are constrained in at least one degree of freedom. In aspects, the ultrasound device and the surgical device are permitted to move in at least one degree of freedom. In other aspects, the ultrasound device and the surgical device are constrained in all degrees of freedom.

In an aspect of the present disclosure, the at least one constrained degree of freedom includes at least one of transverse motion or tilt. Alternatively or additionally, the at least one permitted degree of freedom includes at least one of rotation or longitudinal translation.

In another aspect of the present disclosure, the surgical device is a hysteroscope.

In still another aspect of the present disclosure, the ultrasound device is configured to couple to the inner coupler via an ultrasound device guide disposed on the ultrasound device.

In yet another aspect of the present disclosure, the surgical device is configured to couple to the outer coupler via a surgical device guide disposed on the surgical device.

In still yet another aspect of the present disclosure, the surgical device is configured to move in at least one degree of freedom relative to the surgical device guide when the surgical device is coupled to the surgical device guide.

In another aspect of the present disclosure, the surgical device guide is fixed relative to the inner and outer couplers and the ultrasound device such that the movement of the surgical device relative to the surgical device guide provides the permitted movement of the surgical device relative to the ultrasound device.

Another surgical system provided in accordance with the present disclosure includes a protective cover, an ultrasound device, and a surgical device. The protective cover includes a body, an inner coupler disposed within an interior volume of the body on an interior surface of the body, and an outer coupler disposed on an exterior surface of the body. The ultrasound device is configured for insertion into the interior volume of the body of the protective cover and includes a first guide configured to couple to the inner coupler within the interior volume of the body of the protective cover. The surgical device includes a second guide configured to couple to the outer coupler exteriorly of the protective cover. The inner and outer couplers are engaged to one another with the body of the protective cover disposed therebetween such that, with the first guide coupled to the inner coupler and the second guide coupled to the outer coupler, the ultrasound device and the surgical device are constrained in at least one degree of freedom. In aspects, the ultrasound device and the surgical device are permitted to move in at least one degree of freedom. In other aspects, the ultrasound device and the surgical device are constrained in all degrees of freedom.

In an aspect of the present disclosure, the at least one constrained degree of freedom includes at least one of transverse motion or tilt. Alternatively or additionally, the at least one permitted degree of freedom includes at least one of rotation or longitudinal translation.

In another aspect of the present disclosure, the surgical device is a hysteroscope.

In still another aspect of the present disclosure, the surgical device is configured to move in at least one degree of freedom relative to the second guide.

In yet another aspect of the present disclosure, the inner coupler includes a first engagement interface configured to releasably engage an engagement interface of the first guide and the outer coupler includes a second engagement interface configured to releasably engage an engagement interface of the second guide.

In still yet another aspect of the present disclosure, the first guide is removable from the ultrasound device and/or the second guide is removable from the surgical device.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
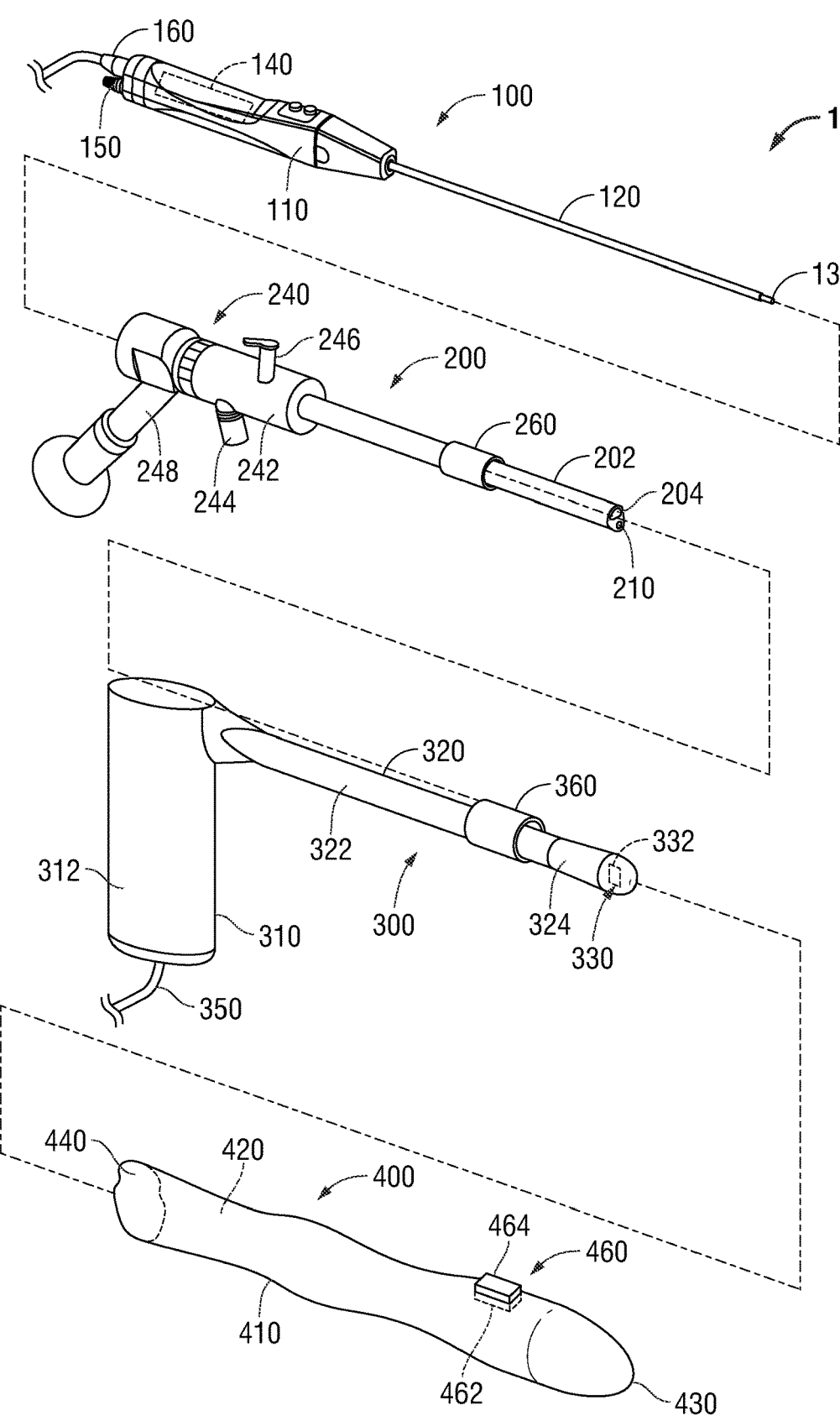
FIG. 1 is an exploded, perspective view of a hysteroscopic system in accordance with the present disclosure including a protective cover, an ultrasound device, a hysteroscope, and a working device.

Referring to FIG. 1, a hysteroscopic system provided in accordance with the present disclosure is shown generally identified by reference numeral 10 including a working device 100, e.g., a tissue resection device, an ablation device, a biopsy device, etc.; a hysteroscope 200; an ultrasound device 300; and a protective cover 400. Ultrasound device 300 is configured for transvaginal insertion into position adjacent to or in abutment with tissue surrounding the cervix. Protective cover 400 is configured for removably covering a portion of ultrasound device 300 to protect ultrasound device 300 and inhibit blood, tissue, and/or other contaminants from contacting ultrasound device 300, thus facilitating cleaning ultrasound device 300 in preparation for subsequent use. Protective cover 400 may be removed and discarded after use, e.g., as a single use, disposable component, or may be configured to be sterilized for repeated use, e.g., as a reusable component. Hysteroscope 200 is configured for insertion through ultrasound device 300 and the cervix into the uterus. Working device 100 is configured for insertion through hysteroscope 200 and into the uterus to perform a surgical procedure in the uterine cavity and/or within the uterine wall. Although described herein with respect to a hysteroscopic system for performing a surgical procedure within the uterus (e.g., within the uterine cavity and/or within the uterine wall), the aspects and features of the present disclosure are also applicable for use in other endoscopic procedures such as ultrasound guided endoscopic surgical procedures.

Working device 100, as noted above, may be a tissue resection device, an ablation device, a biopsy device, or other suitable working device configured for use on or within the uterus. With respect to a tissue resection device, for example, working device 100 includes a housing 110, a shaft 120, a cutting member 130, a drive mechanism 140, an outflow port 150, and a cable 160. Housing 110 houses drive mechanism 140 therein and functions as a handle to enable a user to grasp working device 100. Drive mechanism 140 includes a motor and is operably coupled to cutting member 130 to drive rotation and/or translation of cutting member 130 relative to shaft 120. Drive mechanism 140 is adapted to connect to a control unit (not shown) via cable 160 for powering and controlling the motor, although working device 100 may alternatively be battery powered or manually powered. A suction source (not shown) incorporated into the control unit (not shown), or any other suitable vacuum creating mechanism, may also be provided to facilitate withdrawal of fluid, tissue, and debris through working device 100 and outflow port 150.

Shaft 120 of working device 100 extends distally from housing 110 and, in aspects, is stationary relative to housing 110, although other configurations are also contemplated. Cutting member 130 extends through shaft 120 and is rotatable and/or translatable relative to shaft 120. More specifically, cutting member 130 is operably coupled to drive mechanism 140 for driving the rotation and/or translation of cutting member 130 relative to shaft 120 for cutting and removing tissue. A distal portion of cutting member 130 is exposed via an open distal end of shaft 120 (as shown) and/or a window defined through shaft 120.

In use of working device 100, upon activation, tissue is drawn into shaft 120 and/or cutting member 130. As tissue is drawn into shaft 120 and/or cutting member 130, the tissue is resected via the rotation and/or translation of cutting member 130 relative to shaft 120, thus enabling the resected tissue to be drawn proximally through shaft 120 and/or cutting member 130, along with fluid and debris. The resected tissue, fluid, and debris are drawn proximally through outflow port 150 and outflow tubing (not shown) and, ultimately, to one or more collection canisters of a fluid management system (not shown).

Continuing with reference to FIG. 1, hysteroscope 200 includes an elongated tubular member 202 and a proximal body 240. Elongated tubular member 202 of hysteroscope 200 defines a working channel 204 configured to receive a working device therethrough, e.g., working device 100. Working channel 204 may also serve as a fluid inflow (or outflow) channel. Alternatively or additionally, a separate fluid inflow (or outflow) channel may be provided. Elongated tubular member 200 further includes optics 210 extending therethrough to enable visualization at the distal end of elongated tubular member 202.

Proximal body 240 of hysteroscope 200 includes a housing 242, a light post 244, a valve 246, and an arm 248. Light post 244 extends from housing 242 and is configured to connect to a light source, e.g., to illuminate a distal end of elongated tubular member 202 via one or more fiber optic strands (not shown) coupled to light post 244 and extending through elongated tubular member 202. Valve 246 is disposed in fluid communication with working channel 204 and is configured to enable the selective inflow and/or outflow of fluid to/from working channel 204. In configurations where multiple flow channels are provided, multiple valves may likewise be provided. Arm 248 is configured to connect to an imaging device, e.g., a camera, to capture images received via optics 210 and, thus, enable display of a video image of an internal surgical site as captured by optics 210.

Hysteroscope 200 further includes a guide 260 disposed on elongated tubular member 202. Guide 260, as described in greater detail below, is configured to cooperate with guide 360 of ultrasound device 300 to constrain hysteroscope 200 and ultrasound device 300 relative to one another in at least one degree of freedom while permitting relation motion between hysteroscope 200 and ultrasound device 300 in at least one other degree of freedom.

Referring still to FIG. 1, ultrasound device 300 includes a proximal body 310, a shaft 320 extending distally from proximal body 310, and an ultrasound sensor assembly 330 disposed at a distal end portion 324 of shaft 320. Proximal body 310 of ultrasound device 300 may be configured as a handle including, for example, a pistol style grip 312, although other handle configurations are also contemplated as are non-handle configurations, e.g., for mounting ultrasound device 300 and/or attaching ultrasound device 300 to a surgical robot arm. A cable 350 extends from proximal body 310 to connect ultrasound sensor assembly 330 of ultrasound device 300 to an ultrasound console (not shown), e.g., via wires (not shown) extending from ultrasound sensor assembly 330 through shaft 320, proximal body 310, and cable 350.

Shaft 320 of ultrasound device 300 is configured for transvaginal insertion to position ultrasound sensor assembly 330 in position adjacent to or in abutment with tissue surrounding and/or supporting the cervix, e.g., a vaginal fornix, to enable ultrasound imaging of the cervix, uterus, and/or surrounding tissue using ultrasound sensor assembly 330, as detailed below. A body portion 322 of shaft 320 may define a cylindrical configuration and/or a distal end portion 324 of shaft 320 may be tapered, curved, and/or otherwise atraumatically configured to facilitate atraumatic insertion.

Ultrasound sensor assembly 330 includes one or more ultrasound sensors 332, e.g., ultrasound transducers, to enable ultrasound imaging of tissue. Each ultrasound sensor 332 is configured to emit ultrasound waves, e.g., high frequency sound waves, and to receive echoed waves produced by the reflection of the ultrasound waves against the various tissue structures encountered. The echoed waves received by each ultrasound sensor 332 are output to an image processing unit (not shown), e.g., by way of wires extending through shaft 320, proximal body 310, and cable 350. In aspects, ultrasound sensor assembly 330 may be configured for 2D ultrasound imaging. In other aspects, ultrasound sensor assembly 330 includes a plurality of ultrasound sensors 332 angled relative to one another and/or forming an ultrasound sensor array that defines a portion of a circle, a portion of a polygon, a partially polygonal, partially arcuate configuration, or other suitable configuration to enable reconstruction of a 3D ultrasound image therefrom for 3D ultrasound imaging. Regardless of the particular configuration, ultrasound sensor assembly 330 enables ultrasound imaging of tissue, e.g., the cervix, uterus, and/or surrounding tissue.

Ultrasound device 300 further includes a guide 360 disposed on shaft 320. Guide 360, as described in greater detail below, is configured to cooperate with guide 260 of hysteroscope 200 to constrain hysteroscope 200 and ultrasound device 300 relative to one another in at least one degree of freedom while permitting relation motion between hysteroscope 200 and ultrasound device 300 in at least one other degree of freedom.

With continued reference to FIG. 1, protective cover 400, as noted above, is configured for removably covering a portion of ultrasound device 300 to protect ultrasound device 300, thus facilitating cleaning ultrasound device 300 in preparation for subsequent use. More specifically, protective cover 400 may be configured as a sterile barrier or other suitable cover for removably covering ultrasound sensor assembly 330 and at least a portion of shaft 320 of ultrasound device 300 to maintain a sterile surgical field and/or to protect ultrasound device 300. That is, protective cover 400 may be configured to inhibit blood, tissue, and/or other contaminants from contacting ultrasound device 300, thus facilitating cleaning ultrasound device 300 in preparation for subsequent use. In aspects, protective cover 400 is formed from a flexible and/or transparent material.

Protective cover 400 generally includes a body 410 defining an interior volume 420 and including a closed distal end 430 and an open proximal end 440. Open proximal end 440 is configured to permit insertion of ultrasound device 300, led by ultrasound sensor assembly 330, through open proximal end 440 and into interior volume 420 of body 410. Ultrasound device 300 may be inserted through interior volume 420 until ultrasound sensor assembly 330 is positioned adjacent to and/or abuts an internal surface of closed distal end 430 of body 410. In this position, protective cover 400 may cover at least the portion of ultrasound device 300 configured to be inserted into a patient (e.g., ultrasound sensor assembly 330 and at least a portion (or the entirety) of shaft 320). In aspects, protective cover 400 may cover the entirety of ultrasound device 300, thereby enclosing ultrasound device 300 within interior volume 420.

Protective cover 400 further includes a guide coupling assembly 460. Guide coupling assembly 460 includes an inner coupler 462 and an outer coupler 464 and, as described in greater detail below, is configured to operably couple guide 260 of hysteroscope 200 and guide 360 of ultrasound device 300 with one another to constrain hysteroscope 200 and ultrasound device 300 relative to one another in at least one degree of freedom while permitting relation motion between hysteroscope 200 and ultrasound device 300 in at least one other degree of freedom.

Figures 2A, 2B:
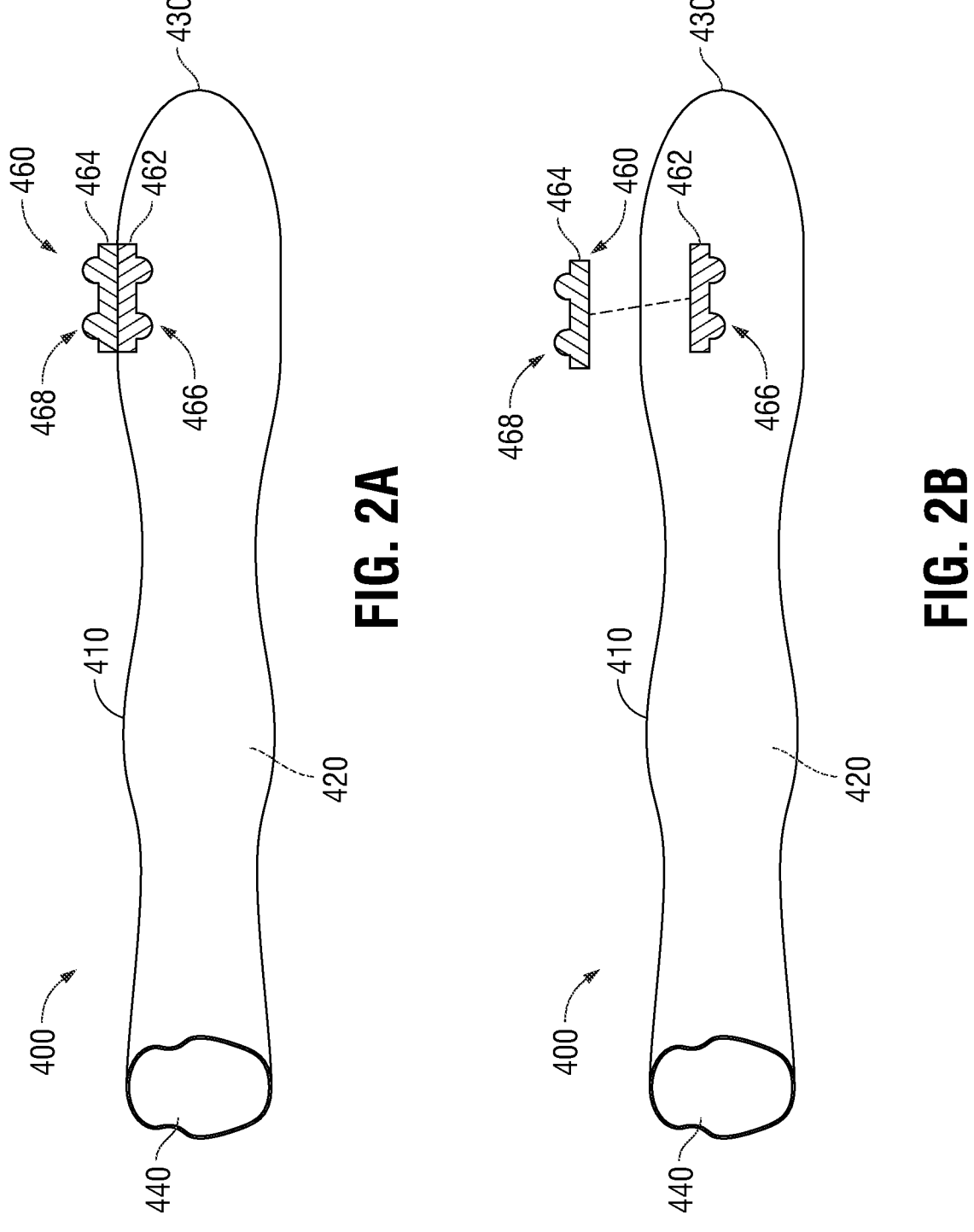
FIG. 2A is a side view of the protective cover of the hysteroscopic system of FIG. 1.
FIG. 2B is an exploded view of the protective cover of the hysteroscopic system of FIG. 1.

Referring to FIGS. 2A and 2B, in conjunction with FIG. 1, guide coupling assembly 460 is shown positioned towards closed distal end 430 of body 410 of protective cover 400. However, guide coupling assembly 460 may be disposed at any suitable position along body 410 of protective cover 400. Guide coupling assembly 460, as noted above, includes inner coupler 462 and outer coupler 464. Inner coupler 462 is disposed within interior volume 420 of body 410 of protective cover 400 while outer coupler 464 is disposed on an exterior surface of body 410 of protective cover 400 such that body 410 of protective cover 400 extends between inner coupler 462 and outer coupler 464. Whereas body 410 of protective cover 400 may be formed from a flexible material, inner and outer couplers 462, 464 may be formed from substantially rigid materials, although other configurations are also contemplated.

Inner and outer couplers 462, 464 may be engaged with one another, with body 410 of protective cover 400 disposed therebetween, to thereby secure inner and outer couplers 462, 464 relative to one another and body 410. Inner and outer couplers 462, 464 may be engaged (with protective cover 400 disposed therebetween) in any suitable manner such as, for example, via mechanical engagement (e.g., snap fitting), adhesion, ultrasonic welding, etc., and may be permanently engaged or removably engagable. As an alternative to inner and outer couplers 462, 464 being engaged with one another (with protective cover 400 disposed therebetween), inner and outer couplers 462, 464 may be engaged with body 410 of protective cover 400 but spaced apart or otherwise separated from one another. Further, in aspects, plural pairs of inner and outer couplers 462, 464 may be provided such as, for example, pairs of inner and outer couplers 462, 464 spaced apart along at least a portion of a length of body 410 of protective cover 400.

Inner coupler 462 includes an inwardly facing engagement interface 466 and outer coupler 464 includes an outwardly facing engagement interface 468. Engagement interfaces 466, 468 may be similar or different from one another and may each include one or more mechanical interfaces, e.g., a male connector, female connector, snap fit component, hook and loop fastener component, etc. Alternatively or additionally, engagement interfaces 466, 468 may include one or more magnetic interfaces, adhesive interfaces, other suitable interfaces, or combinations of interfaces.

Engagement interface 466 is configured to engage engagement interface 366 (FIGS. 3A and 3B) of guide 360 to thereby constrain guide 360 relative to inner coupler 462 in at least one degree of freedom. In aspects, the engagement between guide 360 and inner coupler 462 constrains guide 360 in all degrees of freedom relative to inner coupler 462, thereby substantially fixing guide 360 relative to inner coupler 462 and, thus, relative to protective cover 400. In other aspect, the engagement between guide 360 and inner coupler 462 enables movement of guide 360 relative to inner coupler 462 (and, thus, protective cover 400) in at least one degree of freedom.

Engagement interface 468 is configured to engage engagement interface 268 (FIGS. 5A and 5B) of guide 260 to thereby constrain guide 260 relative to outer coupler 464 in at least one degree of freedom. In aspects, the engagement between guide 260 and outer coupler 464 constrains guide 260 in all degrees of freedom relative to outer coupler 464, thereby substantially fixing guide 260 relative to outer coupler 464 and, thus, relative to protective cover 400. In other aspects, the engagement between guide 260 and outer coupler 464 enables movement of guide 260 relative to outer coupler 464 (and thus, protective cover 400) in at least one degree of freedom.

Figure 3A:
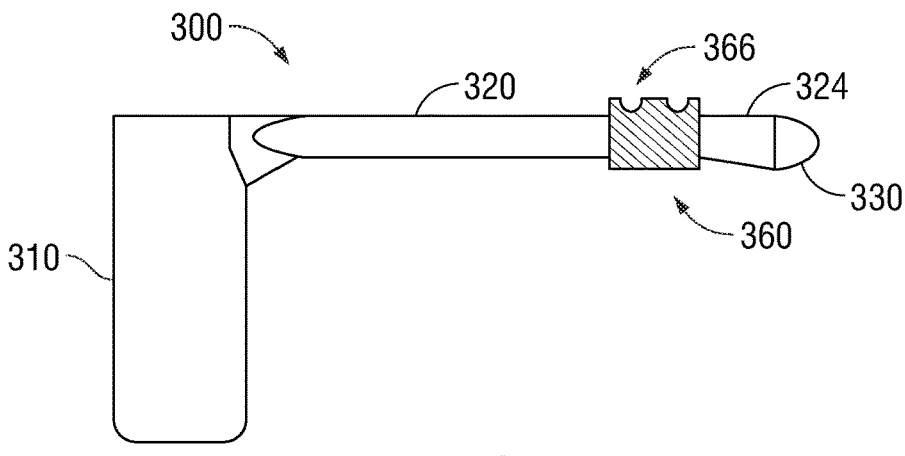
FIG. 3A is a side view of the ultrasound device of the hysteroscopic system of FIG. 1 including an ultrasound device guide engaged thereon.
Figure 3B:
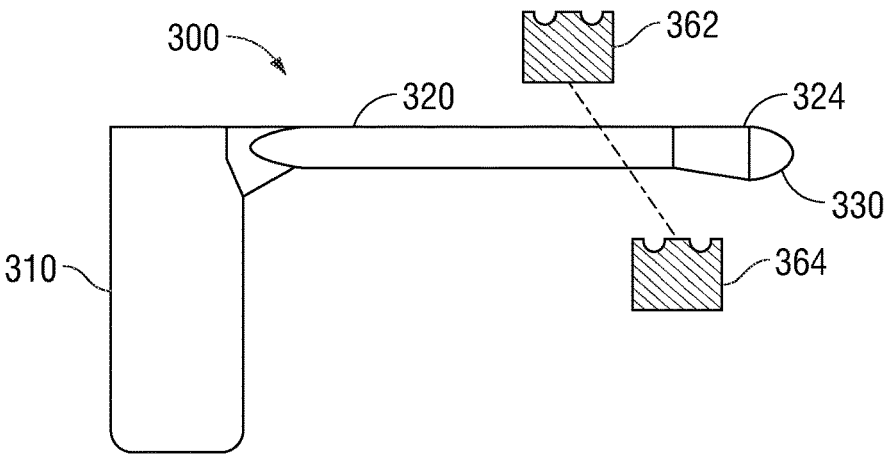
FIG. 3B is an exploded view of the ultrasound device and ultrasound device guide of the hysteroscopic system of FIG. 1.

With reference to FIGS. 3A and 3B, as noted above, ultrasound device 300 includes a guide 360 disposed on shaft 320. Guide 360 may be configured as a collar (as shown) or any other suitable guide. Guide 360 may be rotatably and/or translationally fixed relative to shaft 320 of ultrasound device 300 or may be configured to both rotate and translate relative to shaft 320 of ultrasound device 300. Further, guide 360 may be permanently disposed on shaft 320 or may be removable from shaft 320. Guide 360 may include first and second guide components 362, 364 configured to engage one another with shaft 320 of ultrasound device 300 disposed therebetween to engage guide 360 about shaft 320. Alternatively, guide 360 may be configured for positioning about shaft 320 in any other suitable manner, including sliding guide 360 over distal end 324 of shaft 320 and onto shaft 320.

Referring also to FIGS. 1-2B, guide 360 includes an engagement interface 366 configured to engage engagement interface 466 of inner coupler 462 of guide coupling assembly 460 of protective cover 400 to thereby constrain guide 360 relative to inner coupler 462 and, thus, protective cover 400 in at least one degree of freedom. In aspects, the engagement between guide 360 and inner coupler 462 constrains guide 360 in all degrees of freedom relative to inner coupler 462, thereby substantially fixing guide 360 relative to inner coupler 462 and, thus, protective cover 400. In other aspects, the engagement between guide 360 and inner coupler 462 enables movement of guide 360 relative to inner coupler 462 and, thus, protective cover 400 in at least one degree of freedom, e.g., rotation and/or translation. Engagement interface 366 is complementary to engagement interface 466, thus enabling engagement and, in aspects, releasable engagement, therebetween. Engagement interface 366 may include one or more mechanical interfaces, e.g., a male connector, female connector, snap fit component, hook and loop fastener component, etc. Alternatively or additionally, engagement interface 366 may include one or more magnetic interfaces, adhesive interfaces, other suitable interfaces, or combinations of interfaces.

With engagement interfaces 366, 466 engaged with one another, thereby engaging guide 360 and inner coupler 462 relative to one another, shaft 320 of ultrasound device 300 is constrained in at least one degree of freedom relative to inner coupler 462 and protective cover 400. In aspects, shaft 320 of ultrasound device 300 is constrained in all degrees of freedom relative to inner coupler 462 and protective cover 400. Alternatively, shaft 320 of ultrasound device 300 is movable in at least one degree of freedom relative to inner coupler 462 and protective cover 400, e.g., rotationally and/or translationally.

Figure 4:
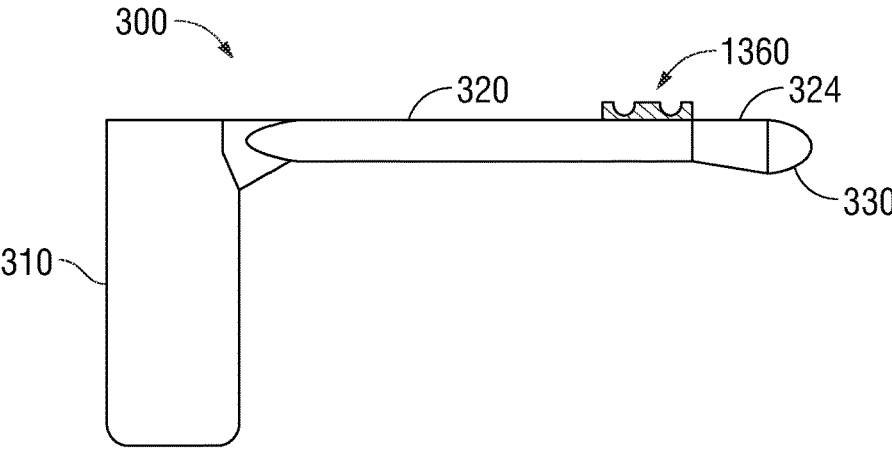
FIG. 4 is a side view of the ultrasound device of the hysteroscopic system of FIG. 1 including an integral ultrasound device guide.

Turning to FIG. 4, in aspects, ultrasound device 300 may include guide 1360 integrally formed with shaft 320. That is, rather than a separate guide, guide 1360 may be part of ultrasound device 300. Guide 1360 may be fixed relative to shaft 320 or movable, e.g., translatable and/or rotatable, relative to shaft 320. Guide 1360 may otherwise be similar to and include any of the features of guide 360 (FIGS. 3A and 3B), as detailed above.

Figure 5A:
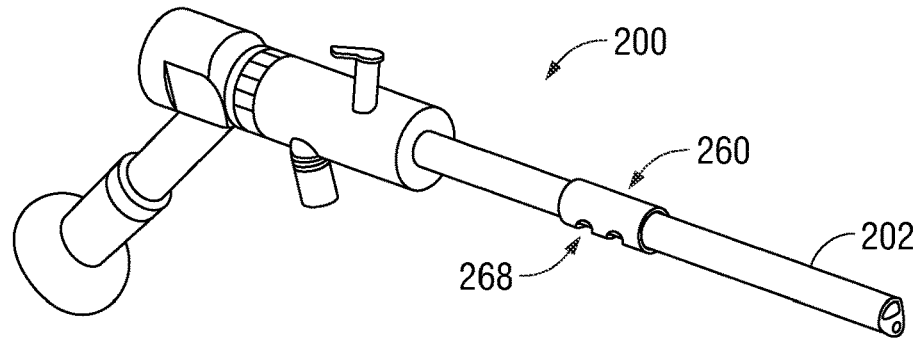
FIG. 5A is a perspective view of the hysteroscope of the hysteroscopic system of FIG. 1 including a hysteroscope guide disposed thereon.
Figure 5B:
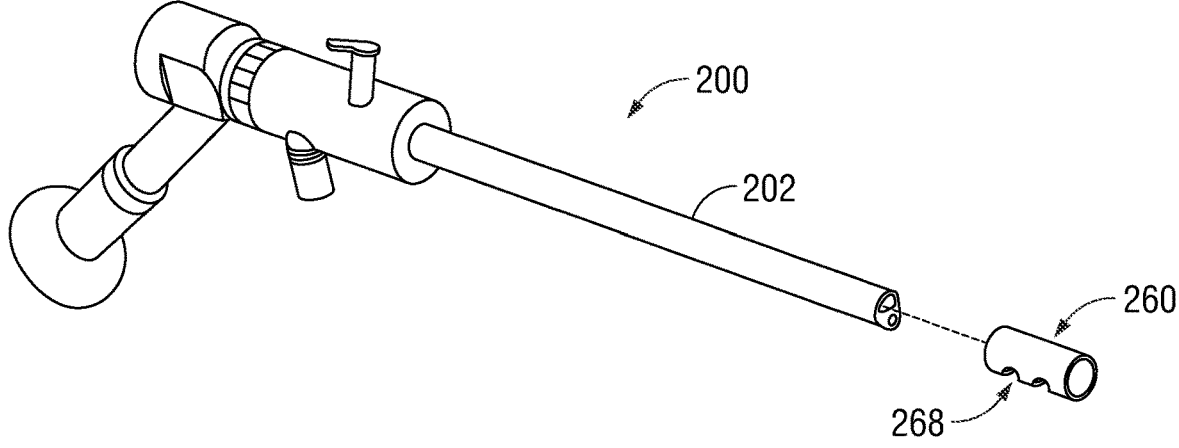
FIG. 5B is a perspective view illustrating positioning of the hysteroscope guide of the hysteroscopic system of FIG. 1 on the hysteroscope of the hysteroscopic system of FIG. 1.

Referring to FIGS. 5A and 5B, as noted above, hysteroscope 200 includes a guide 260 disposed on elongated tubular member 202. Guide 260 may be configured as a collar (as shown) or any other suitable guide. Guide 260 may be rotatably and/or translationally fixed relative to elongated tubular member 202 of hysteroscope 200 or may be configured to both rotate and translate relative to elongated tubular member 202 of hysteroscope 200. Further, guide 260 may be permanently disposed on elongated tubular member 202 or may be removable from elongated tubular member 202. Guide 260 may be configured to slide over the distal end of elongated tubular member 202 onto elongated tubular member 202. Alternatively, guide 260 may be configured for positioning about elongated tubular member 202 in any other suitable manner.

Referring also to FIGS. 1-2B, guide 260 includes an engagement interface 268 configured to engage engagement interface 468 of outer coupler 464 of guide coupling assembly 460 of protective cover 400 to thereby constrain guide 260 relative to outer coupler 464 and thus, protective cover 400 in at least one degree of freedom. In aspects, the engagement between guide 260 and outer coupler 464 constrains guide 260 in all degrees of freedom relative to outer coupler 464, thereby substantially fixing guide 260 relative to outer coupler 464. In other aspects, the engagement between guide 260 and outer coupler 464 enables movement of guide 260 relative to outer coupler 464 in at least one degree of freedom, e.g., rotation and/or translation. Engagement interface 268 is complementary to engagement interface 468, thus enabling engagement and, in aspects, releasable engagement, therebetween. Engagement interface 268 may include one or more mechanical interfaces, e.g., a male connector, female connector, snap fit component, hook and loop fastener component, etc. Alternatively or additionally, engagement interface 268 may include one or more magnetic interfaces, adhesive interfaces, other suitable interfaces, or combinations of interfaces.

With engagement interfaces 268, 468 engaged with one another, thereby engaging guide 260 and outer coupler 464 relative to one another, elongated tubular member 202 of hysteroscope 200 is constrained in at least one degree of freedom relative to outer coupler 464 and protective cover 400. In aspects, elongated tubular member 202 of hysteroscope 200 is permitted to rotate and/or translate relative to outer coupler 464 and protective cover 400 (FIGS. 2A and 2B) but is constrained in all other degrees of freedom, e.g., transverse motion and tilt.

Figure 6:
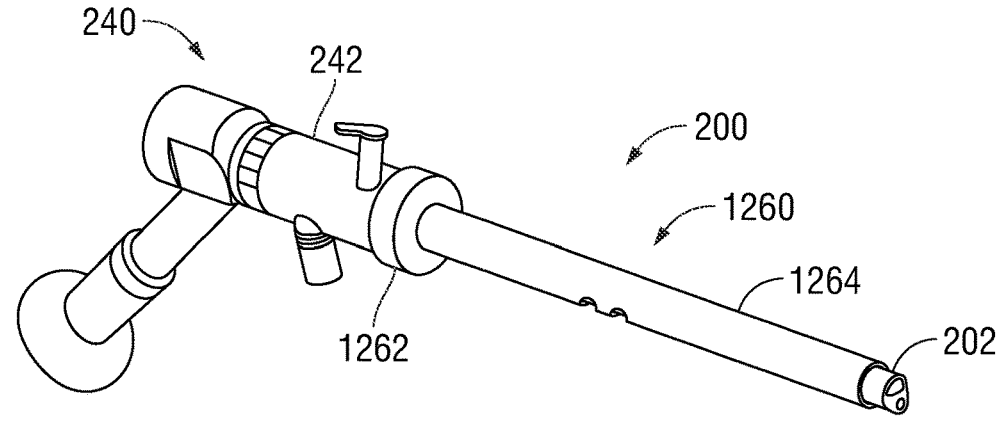
FIG. 6 is a perspective view of the hysteroscope of the hysteroscopic system of FIG. 1 including another hysteroscope guide disposed thereon.

Turning to FIG. 6, in aspects, rather than being formed as a collar or other suitable guide that is disposed about a relatively small portion of elongated tubular member 202 of hysteroscope 200, hysteroscope 200 may include a guide 1260 configured as a sheath disposed about elongated tubular member 202 substantially along an entire length of elongated tubular member 202. In such configurations, guide 1260 may include a proximal hub 1262 configured to releasably engage housing 242 of proximal body 240 of hysteroscope 200 and an elongated distal body 1264 extending distally from proximal hub 1262 about and substantially along the entire length of elongated tubular member 202. Guide 1260 or at least elongated distal body 1264 thereof, may be rotatable relative to hysteroscope 200. Alternatively, guide 1260 may be fixed relative to hysteroscope 200. Further, guide 1260 may provide additional functionality such as, for example, enabling inflow and/or outflow of fluid through an annular space defined between guide 1260 and elongated tubular member 202 of hysteroscope 200. Fluid may enter and/or exit guide 1260, for example, at the proximal end of guide 1260 via a proximal port (not shown) coupled to proximal hub 1262, and, at the distal end of guide 1260 via an open distal end of elongated distal body 1264. Other configurations are also contemplated. Guide 1260 may otherwise be similar to and include any of the features of guide 260 (FIGS. 5A and 5B), as detailed above.

With reference to FIGS. 7A-7E, assembly and use of hysteroscope 200, ultrasound device 300, and protective cover 400 are described. Although necessarily described in a particular order, it is understood that the steps of assembly of hysteroscope 200, ultrasound device 300, and protective cover 400 may be performed in any other suitable order.

Figure 7A:
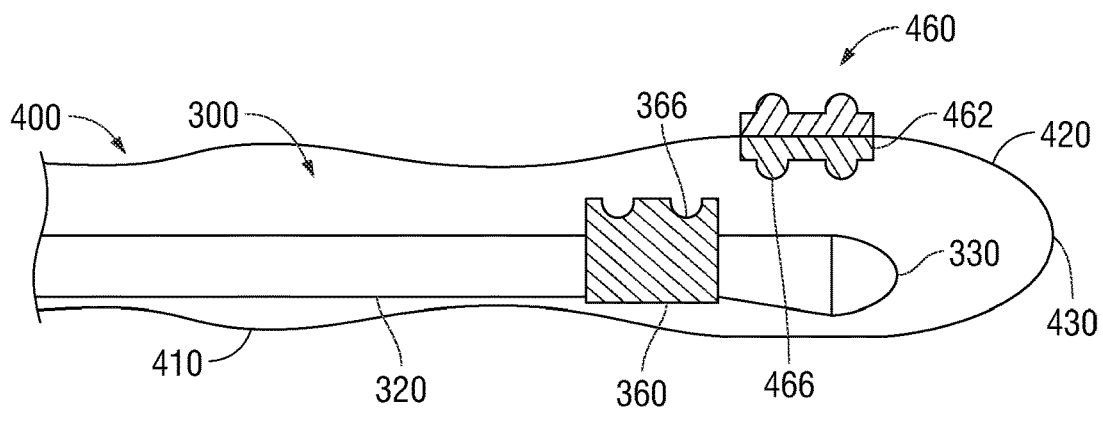
FIGS. 7A-7E are side views progressively illustrating insertion of the ultrasound device into the protective cover, engagement of the ultrasound device with the protective cover, positioning of the hysteroscope relative to the protective cover, coupling of the hysteroscope with the protective cover, and movement of the hysteroscope relative to the protective cover and ultrasound device while coupled thereto, respectively.
Figure 7B:
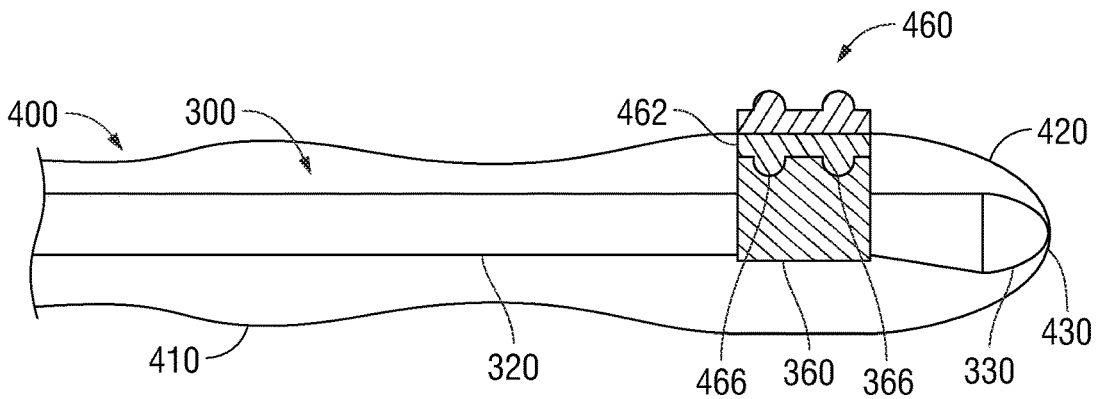

As shown in FIGS. 7A and 7B, with guide 360 disposed on shaft 320 of ultrasound device 300, shaft 320 of ultrasound device 300, led by ultrasound sensor assembly 330, is inserted through open proximal end 440 (FIGS. 2A and 2B) of body 410 of protective cover 400 and is advanced distally through interior volume 420 to closed distal end 430 of body 410 of protective cover 400. Once shaft 320 of ultrasound device 300 is sufficiently inserted into interior volume 420 of body 410 of protective cover 400 such that guide 360 of ultrasound device 300 and inner coupler 462 of guide coupling assembly 460 of protective cover 400 are approximated relative to one another, ultrasound device 300 and/or protective cover 400 may be manipulated to engage engagement interface 366 of guide 360 with engagement interface 466 of inner coupler 462, thereby constraining guide 360 relative to inner coupler 462 in at least one degree of freedom and, thus, constraining shaft 320 of ultrasound device 300 relative to protective cover 400 in at least one degree of freedom.

Figure 7C:
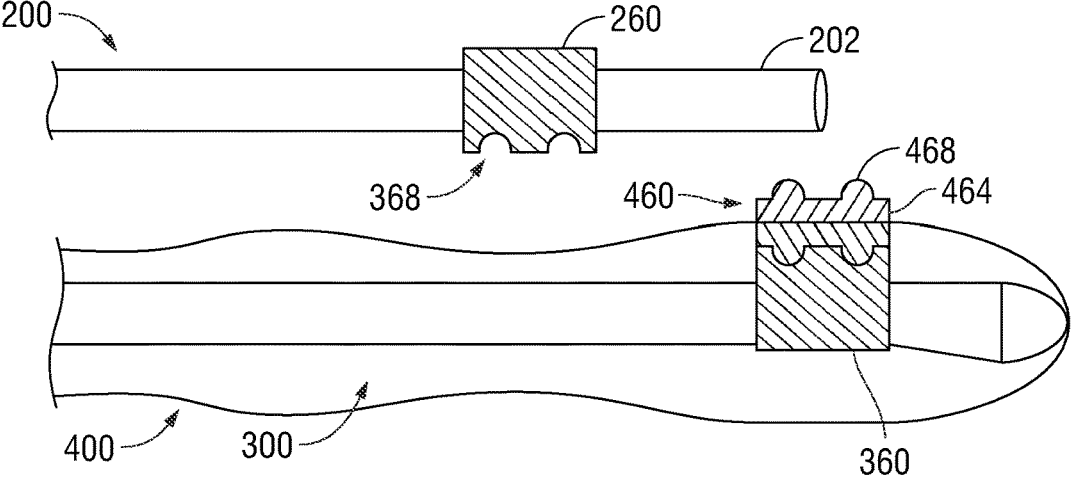
Figures 7D, 7E:
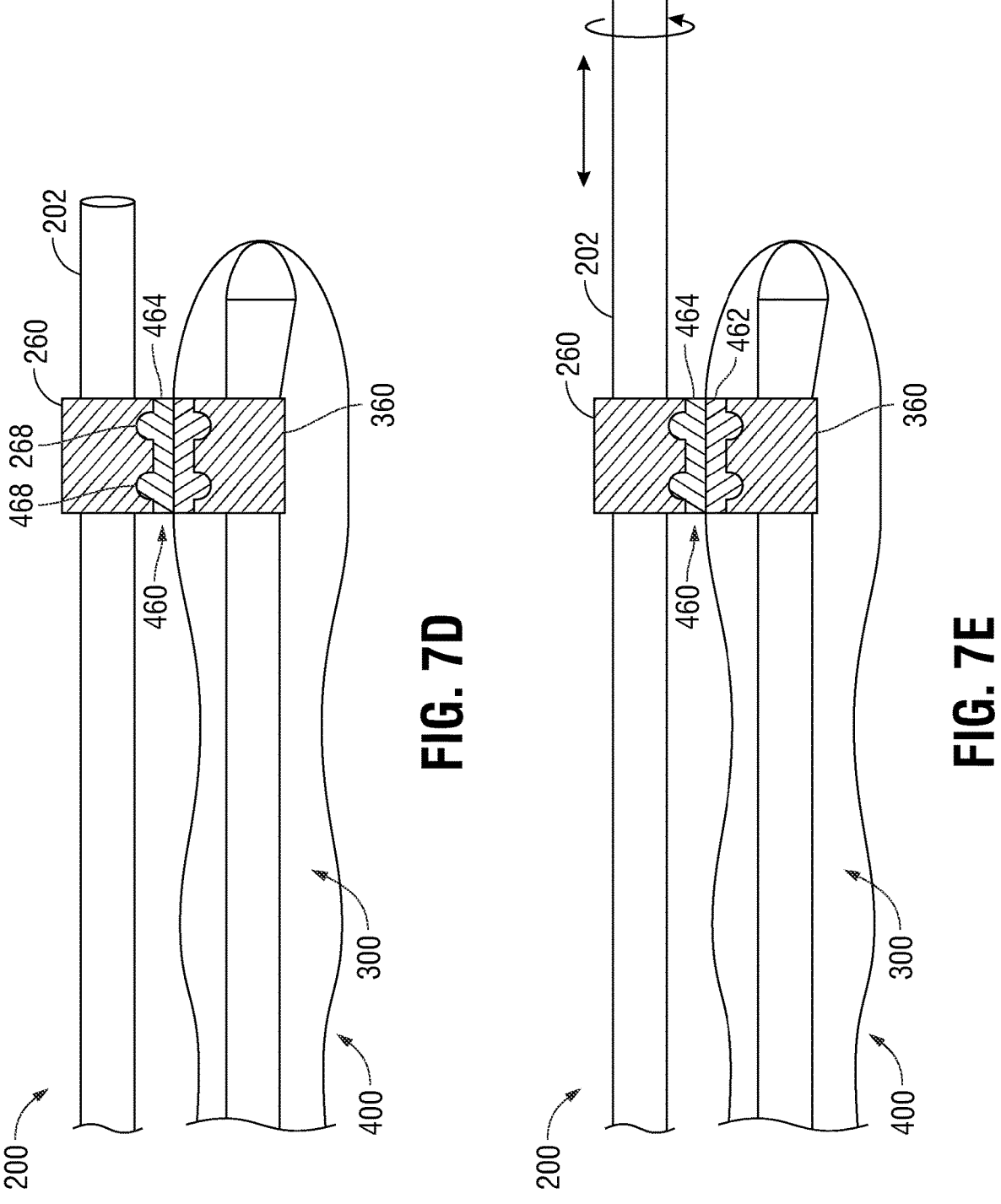

As shown in FIGS. 7C and 7D, with guide 260 disposed on elongated tubular member 202 of hysteroscope 200, elongated tubular member 202 of hysteroscope 200 is advanced distally along an exterior of body 410 of protective cover 400 towards closed distal end 430 of body 410 of protective cover 400. Once elongated tubular member 202 of hysteroscope 200 is sufficiently positioned in this manner such that guide 260 of hysteroscope 200 and outer coupler 464 of guide coupling assembly 460 of protective cover 400 are approximated relative to one another, hysteroscope 200 and/or protective cover 400 may be manipulated to engage engagement interface 268 of guide 260 with engagement interface 468 of outer coupler 464, thereby constraining guide 260 relative to outer coupler 464 in at least one degree of freedom and, thus, constraining elongated tubular member 202 of hysteroscope 200 relative to protective cover 400 in at least one degree of freedom. Further, with both hysteroscope 200 and ultrasound device 300 constrained relative to protective cover 400 in at least one degree of freedom, hysteroscope 200 and ultrasound device 300 are thus constrained relative to one another in at least one degree of freedom. In aspects, hysteroscope 200 and ultrasound device 300 are movable relative to one another in at least one other degree of freedom.

As shown in FIG. 7E, with both hysteroscope 200 and ultrasound device 300 constrained relative to one another in at least one degree of freedom, e.g., inhibiting relative transverse motion and/or tilt motion, hysteroscope 200 and ultrasound device 300 are movable relative to one another in at least one other degree of freedom, e.g., allowing relative rotation and/or translation. However, other constrained and/or unconstrained degrees of freedom between hysteroscope 200 and ultrasound device 300 are also contemplated. By constraining hysteroscope 200 and ultrasound device 300 relative to one another in at least one degree of freedom, hysteroscope 200 (and working device 100 (FIG. 1) inserted therethrough) can be maintained within the imaging plane of ultrasound sensor assembly 330 (FIG. 1) of ultrasound device 300 as hysteroscope 200 (and/or working device 100 (FIG. 1) inserted therethrough) is moved in the at least one unconstrained degree of freedom. Further, guide coupling assembly 460 of protective cover 400 enables the above operable coupling of hysteroscope 200 and ultrasound device 300 with protective cover 400 disposed therebetween and protecting ultrasound device 300 without compromising protective cover 400.

Referring generally to FIGS. 1-7E, in aspects, guide 360 may be integrally formed with inner coupler 462 and/or guide 260 may be integrally formed with outer coupler 464. In configurations where guide 360 is integrally formed with inner coupler 462, shaft 320 of ultrasound device 300 may be inserted into protective cover 400 to releasably engage guide 360, thereby engaging shaft 320 of ultrasound device 300 with inner coupler 462 similarly as detailed hereinabove. In configurations where guide 260 is integrally formed with outer coupler 464, elongated tubular member 202 of hysteroscope 200 may releasably engage guide 260, thereby engaging elongated tubular member 202 of hysteroscope 200 with outer coupler 464 similarly as detailed hereinabove.

Figure 8:
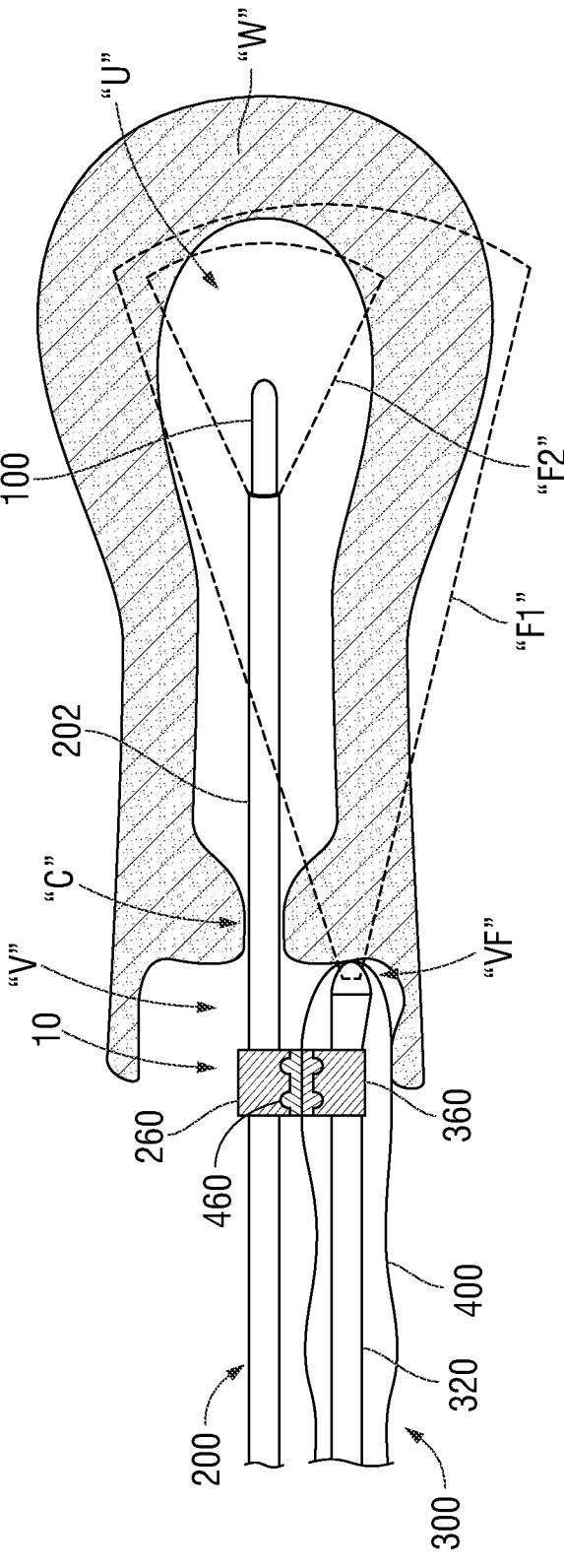
FIG. 8 is a side, partial cross-sectional view of the hysteroscopic system of FIG. 1 in use wherein the ultrasound device is positioned adjacent the cervix with the protective cover engaged about the ultrasound device, the hysteroscope is coupled to the protective cover and extends through the cervix into the uterus, and the working device extends from the hysteroscope into the uterus.

Turning to FIG. 8, hysteroscopic system 10 is shown in use wherein ultrasound sensor assembly 330 and at least a portion of shaft 320 of ultrasound device 300 are disposed within protective cover 400 with guide 360 engaged with guide coupling assembly 460. Ultrasound sensor assembly 330 and at least a portion of shaft 320 of ultrasound device 300, with protective cover 400 disposed thereabout, extends transvaginally through the vaginal canal "V" such that ultrasound sensor assembly 330 is disposed adjacent or in abutment (with protective cover 400 disposed therebetween) with tissue surrounding the cervix "C" such as, for example, a vaginal fornix "VF." In this position, ultrasound sensor assembly 330 defines an ultrasound imaging field of view "F1" that includes at least a portion of the uterus "U" and surrounding tissue.

Elongated tubular member 202 of hysteroscope 200 extends transvaginally through the vaginal canal "V" and the cervix "C" into the uterus "U." In this manner, hysteroscope 200 may be utilized for visualization within the uterus "U," e.g., providing an imaging field of view "F2," together with or separately from the ultrasound imaging. Hysteroscope 200 may also be used for the introduction of fluid into and/or the removal of fluid from the uterus "U" and/or for passage of working device 100, e.g., a tissue resection device, ablation device, biopsy device, etc., therethrough and into the uterus "U" to perform one or more hysteroscopic tasks within the uterus "U" or within the uterine wall "W." Guide 260 of hysteroscope 200 is engaged with guide coupling assembly 460 of protective cover 400 to thereby constrain hysteroscope 200 in at least one degree of freedom relative to ultrasound device 300 while permitting at least one degree of freedom of hysteroscope 200 relative to ultrasound device 300. The constraint of hysteroscope 200 in at least one degree of freedom relative to ultrasound device 300 may ensure at least partial overlap of the imaging fields of view "F1" and "F2" and/or such that at least a portion of hysteroscope 200 and/or working device 100 is maintained within the ultrasound imaging field of view "F1" despite movement of hysteroscope 200 and/or working device 10 relative to ultrasound device 300 in the at least one unconstrained degree of freedom.

Figure 9:
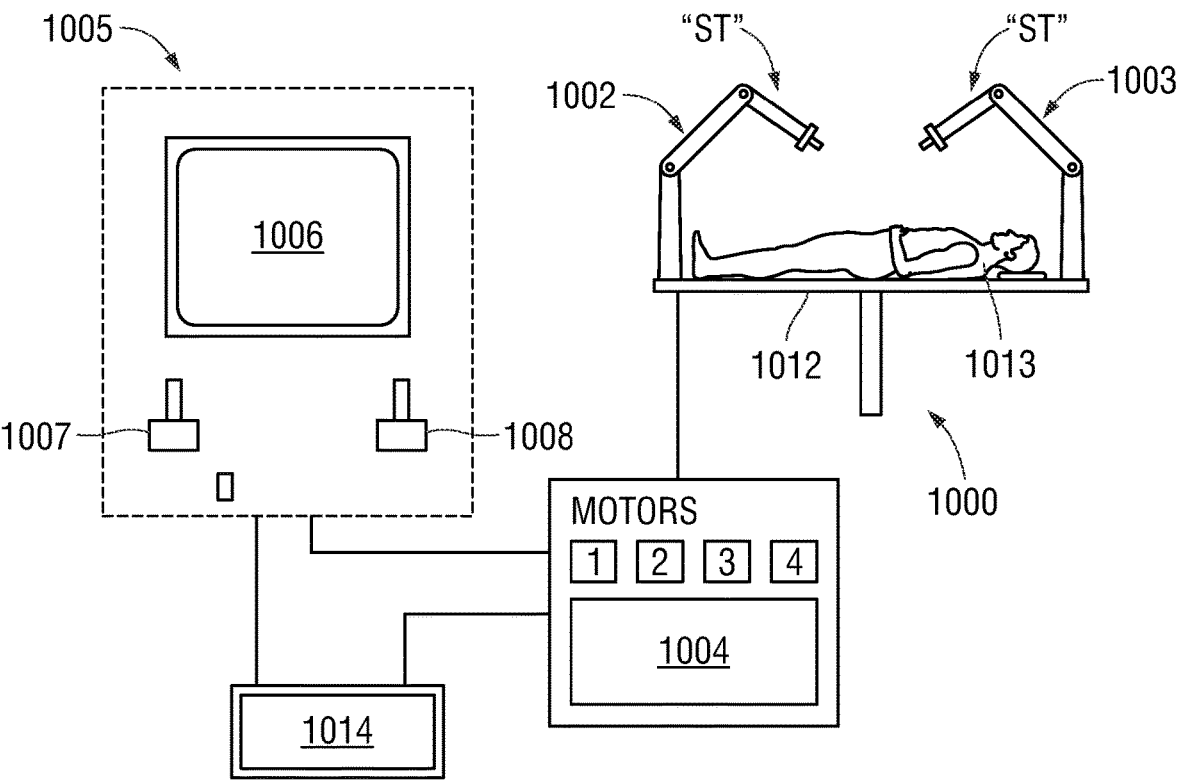
FIG. 9 is a schematic illustration of a robotic surgical system configured for use in accordance with the aspects of the present disclosure.

With reference to FIG. 9, a robotic surgical system 1000 configured for use in accordance with the present disclosure is shown. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003 (although two robot arms are shown, only one or more than two robot arms 1002, 1003 are also contemplated); a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and a mounted device which may be, for example, a surgical tool "ST." With momentary additional reference to FIG. 1, the surgical tools "ST" may include, for example, working device 100, hysteroscope 200, ultrasound device 300, etc., thus providing any of the above detailed functionality of system 10 on a robotic surgical system 1000.

Continuing with reference to FIG. 9, robot arms 1002, 1003 may be driven by electric drives, e.g., motors, connected to control device 1004. The motors, for example, may be rotational drive motors configured to provide rotational inputs to accomplish a desired task or tasks. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Control device 1004, more specifically, may control one or more of the motors based on rotation, e.g., controlling to rotational position using a rotational position encoder (or Hall effect sensors or other suitable rotational position detectors) associated with the motor to determine a degree of rotation output from the motor and, thus, the degree of rotational input provided. Alternatively or additionally, control device 1004 may control one or more of the motors based on torque, current, or in any other suitable manner.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A surgical system, comprising:
   a protective cover including a body, an inner coupler disposed within an interior volume of the body and fixed to an interior surface of the body, and an outer coupler disposed on and fixed to an exterior surface of the body, the inner and outer couplers fixedly engaged with one another;
   an ultrasound device including a proximal housing, a shaft extending distally from the proximal housing, and an ultrasound sensor assembly disposed at a distal end portion of the shaft, at least the ultrasound sensor assembly and a portion of the shaft configured for insertion into the interior volume of the body of the protective cover, the shaft of the ultrasound device configured to couple to the inner coupler within the interior volume of the body of the protective cover; and
   a surgical device configured to couple to the outer coupler exteriorly of the protective cover,
   wherein, with the shaft of the ultrasound device coupled to the inner coupler within the body of the protective cover and the surgical device coupled to the outer coupler exteriorly of the body, the ultrasound device and the surgical device are spaced-apart relative to one another and constrained in at least one degree of freedom while movement of the surgical device relative to the ultrasound device is permitted in at least one other degree of freedom.

2. The surgical system according to claim 1, wherein the at least one constrained degree of freedom includes at least one of transverse motion or tilt.

3. The surgical system according to claim 1, wherein the at least one permitted degree of freedom includes at least one of rotation or longitudinal translation.

4. The surgical system according to claim 1, wherein the surgical device is a hysteroscope.

5. The surgical system according to claim 1, wherein the shaft of the ultrasound device is configured to couple to the inner coupler via an ultrasound device guide disposed on the shaft of the ultrasound device.

6. The surgical system according to claim 1, wherein the surgical device is configured to couple to the outer coupler via a surgical device guide disposed on the surgical device.

7. The surgical system according to claim 6, wherein the surgical device is configured to move in at least one degree of freedom relative to the surgical device guide when the surgical device is coupled to the surgical device guide.

8. The surgical system according to claim 7, wherein the surgical device guide is fixed relative to the inner and outer couplers and the ultrasound device such that the movement of the surgical device relative to the surgical device guide provides the permitted movement of the surgical device relative to the ultrasound device.

9. A surgical system, comprising:
   a protective cover including a body, an inner coupler disposed within an interior volume of the body and fixed to an interior surface of the body, and an outer coupler disposed on and fixed to an exterior surface of the body, the inner and outer couplers fixedly engaged with one another;
   an ultrasound device including a proximal housing, a shaft extending distally from the proximal housing, and an ultrasound sensor assembly disposed at a distal end portion of the shaft, at least the ultrasound sensor assembly and a portion of the shaft configured for insertion into the interior volume of the body of the protective cover, the shaft of the ultrasound device including a first guide configured to couple to the inner coupler within the interior volume of the body of the protective cover; and
   a surgical device including a second guide configured to couple to the outer coupler exteriorly of the protective cover,
   wherein, with the first guide coupled to the inner coupler within the body of the protective cover and the second guide coupled to the outer coupler exteriorly of the protective cover, the ultrasound device and the surgical device are spaced-apart relative to one another and constrained in at least one degree of freedom while movement of the surgical device relative to the ultrasound device is permitted in at least one other degree of freedom.

10. The surgical system according to claim 9, wherein the at least one constrained degree of freedom includes at least one of transverse motion or tilt.

11. The surgical system according to claim 9, wherein the at least one permitted degree of freedom includes at least one of rotation or longitudinal translation.

12. The surgical system according to claim 9, wherein the surgical device is a hysteroscope.

13. The surgical system according to claim 9, wherein the surgical device is configured to move in at least one degree of freedom relative to the second guide.

14. The surgical system according to claim 9, wherein the inner coupler includes a first engagement interface configured to releasably engage an engagement interface of the first guide and wherein the outer coupler includes a second engagement interface configured to releasably engage an engagement interface of the second guide.

15. The surgical system according to claim 9, wherein at least one of: the first guide is removable from the ultrasound device, or the second guide is removable from the surgical device.

*     *     *     *     *